United States Patent
Warrier et al.

(10) Patent No.: US 9,238,666 B2
(45) Date of Patent: Jan. 19, 2016

(54) PHOSPHORAMIDIC ACID PRODRUGS OF 5-[5-PHENYL-4-(PYRIDIN-2-YLMETHYL AMINO)QUINAZOLIN-2-YL] PYRIDINE-3-SULFONAMIDE

(71) Applicant: BRISTOL-MYERS SQUIBB COMPANY, Princeton, NJ (US)

(72) Inventors: Jayakumar S. Warrier, Bangalore (IN); Navnath Dnyanoba Yadav, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/406,543

(22) PCT Filed: Jun. 10, 2013

(86) PCT No.: PCT/US2013/044882
§ 371 (c)(1),
(2) Date: Dec. 9, 2014

(87) PCT Pub. No.: WO2013/188254
PCT Pub. Date: Dec. 19, 2013

(65) Prior Publication Data
US 2015/0175641 A1 Jun. 25, 2015

Related U.S. Application Data

(60) Provisional application No. 61/657,913, filed on Jun. 11, 2012.

(51) Int. Cl.
| | | |
|---|---|---|
| *C07F 9/6512* | (2006.01) | |
| *C07D 401/14* | (2006.01) | |
| *C07F 9/6558* | (2006.01) | |
| *A61K 31/675* | (2006.01) | |

(52) U.S. Cl.
CPC ............ *C07F 9/65128* (2013.01); *A61K 31/675* (2013.01); *C07D 401/14* (2013.01); *C07F 9/65583* (2013.01)

(58) Field of Classification Search
CPC ..... A01N 43/54; A61K 31/517; C07D 401/02
USPC ........................................ 514/266.2; 544/284
See application file for complete search history.

(56) References Cited

U.S. PATENT DOCUMENTS 8,575,184 B2    11/2013   Johnson et al.
2014/0031345 A1  1/2014   Johnson et al.

FOREIGN PATENT DOCUMENTS

| WO | WO 2004/058778 | 7/2004 |
| WO | WO 2006/028590 A1 | 3/2006 |
| WO | WO 2011/028741 | 3/2011 |
| WO | WO 2011/029054 | 3/2011 |
| WO | WO 2011/082337 | 7/2011 |

OTHER PUBLICATIONS

Almansa, C. et al., "New Water-Soluble Sulfonylphosphoramidic Acid Derivatives of the COX-2 Selective Inhibitor Cimicoxib. A Novel Approach to Sulfonamide Prodrugs", Journal of Medicinal Chemistry, vol. 47, No. 22, pp. 5579-5582 (2004).
Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

*Primary Examiner* — Paul V Ward
(74) *Attorney, Agent, or Firm* — Mary K. VanAtten

(57) ABSTRACT

A compound of structural formula (I), wherein R is H or —PO3H or a pharmaceutically acceptable salt form thereof. The compounds are useful as inhibitors of potassium channel function and in the treatment and prevention of arrhythmia, $I_{Kur}$-associated disorders, and other disorders mediated by ion channel function.

(I)

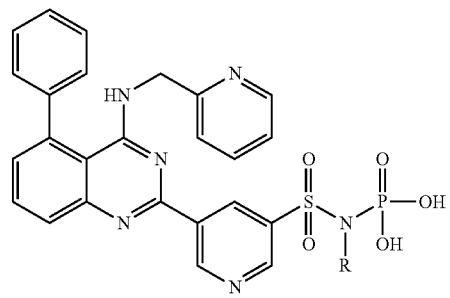

16 Claims, No Drawings

PHOSPHORAMIDIC ACID PRODRUGS OF 5-[5-PHENYL-4-(PYRIDIN-2-YLMETHYL AMINO)QUINAZOLIN-2-YL] PYRIDINE-3-SULFONAMIDE

CROSS REFERENCES TO RELATED APPLICATIONS

This application is a 371 of International Application No. PCT/US2013/044882, filed on Jun. 10, 2013, which claims the benefit of U.S. Provisional Applications Ser. No. 61/657,913 filed on Jun. 11, 2012, which is incorporated herein by reference.

FIELD OF THE DISCLOSURE

The present disclosure generally relates to prodrugs and more specifically towards the phosphoramidic acid prodrugs, its compositions and methods of using such compounds in the treatment and prevention of arrhythmia, $I_{Kur}$-associated disorders, and other disorders mediated by ion channel function.

BACKGROUND OF THE DISCLOSURE

Atrial fibrillation (AF) is the most frequently observed type of cardiac arrhythmia and is generally identified clinically when taking a pulse and can be further confirmed with an electrocardiogram (ECG). AF causes cardiogenic cerebral embolism, and is therefore recognized as an arrhythmia that greatly affects vital prognoses and quality of life. It is known that the onset of AF increases with age, and that repeated AF strokes lead to chronic AF (*The Journal of American Medical Association*, 285:2370-2375 (2001) and *Circulation*, 114:119-123 (2006)).

The cardiac repolarization process is regulated by several outward currents, of which the ultrarapid delayed rectifier potassium current (IKur) is thought to play a major role. This current is absent in the ventricles and hence represents a suitable target for selectively modulating action potentials (APs) in the atria (Wang. Z. et al., "Sustained depolarization-induced outward current in human atrial myocytes: evidence for a novel delayed rectifier K+ current similar to $K_v1.5$ cloned channels currents", *Circ Res.*, 73:1061-1076 (1993); Courtemanche, M. et al., "Ionic targets for drug therapy and atrial fibrillation-induced electrical remodeling: insights from a mathematical model", *Cardiovasc Res.*, 42:477-489 (1999); and Nattel, S., "New ideas about atrial fibrillation 50 years on", *Nature*, 415:219-226 (2002)).

The ultra-rapidly activating delayed rectifier K+ current ($I_{Kur}$) is believed to represent the native counterpart to a cloned potassium channel designated $K_v1.5$ and, while present in human atrium, it appears to be absent in human ventricle. Additionally, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. An improved agent for the prevention and treatment of AF should prolong atrial refractory period and maintain normal sinus rate without affecting the ventricle.

PCT publication number WO 2011/028741 A1 discloses compounds useful as inhibitors of potassium channel function which are used for the treatment and prevention of arrhythmia, $I_{Kur}$-associated disorders. The contents of this PCT publication are incorporated herein by reference.

The $I_{Kur}$ inhibitor compounds may show pH-dependent solubility and pH-dependent bioavailability. To mitigate the long-term developability risk of reduced bioavailability in patients with concomitant gastric acid suppression therapies, it would be ideal to have a prodrug that would mitigate this property.

Prodrugs are new chemical entities which upon administration to the patient, regenerate the respective parent molecule within the body. Prodrug strategies or methodologies can be used to markedly enhance properties of a drug or to overcome an inherent deficiency in the pharmaceutical or pharmacokinetic properties of a drug. Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

A myriad of Prodrug strategies exist which provide choices in modulating the conditions for regeneration of the parent drug, the physical, pharmaceutical or pharmacokinetic properties of the Prodrug, and the functionality to which the Prodrug modifications may be attached. The identification of prodrugs with desired properties is often difficult and is not straightforward.

SUMMARY OF THE DISCLOSURE

Accordingly, the present disclosure provides compounds of structural formula I

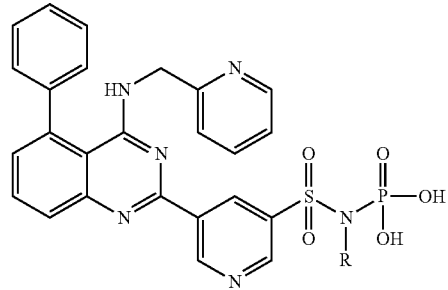

Formula I wherein R is H or —$PO_3H$ or a pharmaceutically acceptable salt form thereof.

Also, the disclosure provides for a pharmaceutical composition comprising a therapeutically effective amount of at least one compound of structural formula I.

Further, the present disclosure provides for a method of treating or preventing cardiac arrhythmia comprising administering to a patient in need thereof an effective amount of at least one compound of structural formula I.

Furthermore, the disclosure provides a method of controlling heart rate and a method of treating $I_{Kur}$-associated condition comprising administering to a patient in need thereof an effective amount of at least one compound of structural formula I.

By use of a respective effective amount of at least one compound described herein, provided are methods of treating (including ameliorating) or preventing arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Also included are compounds for the use in therapy. Also included are compounds for use in therapy, wherein the therapy is treating (including ameliorating) or preventing arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate. And further, wherein the therapy is treating or preventing cardiac arrhythmia.

Also included are the use of the compounds of formula I, II or III in the preparation of a medicament for the treatment or prevention of arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate. And further, for the treatment of prevention of cardiac arrhythmia.

DETAILED DESCRIPTION

Listed below are definitions of various terms used to describe the present disclosure. These definitions apply to the terms as they are used throughout the specification (unless they are otherwise limited in specific instances) either individually or as part of longer group.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ or D and $^3H$ or T, carbon such as $^{11}C$, $^{13}C$, and $^{14}C$, chlorine, such as $^{36}Cl$, fluorine such as $^{18}F$, iodine, such as $^{123}I$ and $^{125}I$, nitrogen, such as $^{13}N$ and $^{15}N$, oxygen, such as $^{15}O$, $^{17}O$, and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$ or D, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{18}F$, $^{15}O$, and $^{13}N$, can be useful in Positron Emission Topography (PET) studies for examining substrate receptor occupancy.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

Treating" or "treatment" as used herein covers the treatment, prophylaxis, and/or reducing the risk, of a disease or disorder described herein, or treatment, prophylaxis, or reducing the risk of a symptom of a disease or disorder, in a subject, such as a human, and includes:

i. inhibiting a disease or disorder, i.e., arresting its development; or ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

The terms "including", "such as", "for example" and the like are intended to refer to exemplary embodiments and not to limit the scope of the present invention.

The compounds described herein which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

While the salts of the compounds of the present invention are illustrated as having negative charge (and therefore, are missing a hydrogen) on certain atoms, it is to be understood that the negative charge may be present on another of the atoms of substituent, and that one of the other hydrogen atoms may be removed (tautomer of the anion). Furthermore, the negative charge may be present at different atoms on different molecules, thereby forming a mixture of anions. The present invention is not intended to be limited to the specific depiction of the anionic charge shown on the compounds.

First embodiment of the present disclosure, provides compound of structural formula I

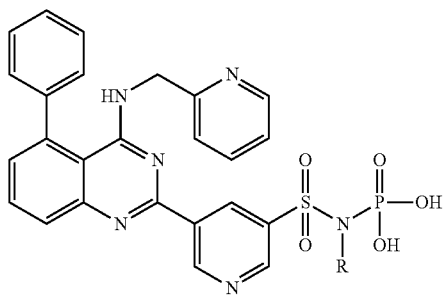

Formula I wherein R is H, or pharmaceutically acceptable salt thereof

In second embodiment of the present disclosure, provides a compound having structural formula II

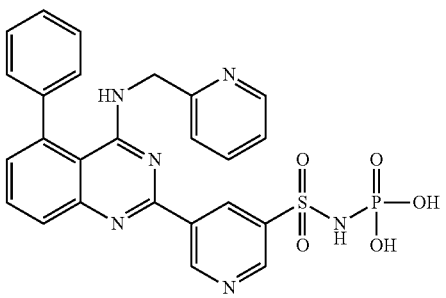

Formula II

In third embodiment of the present disclosure, provides salts of structural formula I and structural formula II, wherein the pharmaceutically acceptable salt is $Na^{(+)}$, $K^{(+)}$, $Ca^{(+2)}$, $Mg^{(+2)}$, or $(NH_3^{(+)}-CH_2-C(CH_2OH)_3)$.

In fourth embodiment of the present disclosure, provides compounds selected from a group consisting of

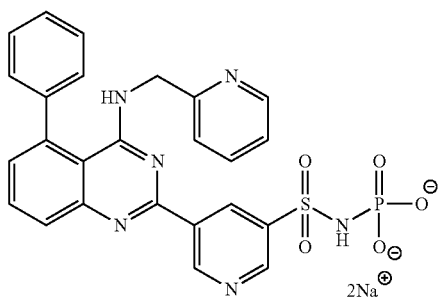

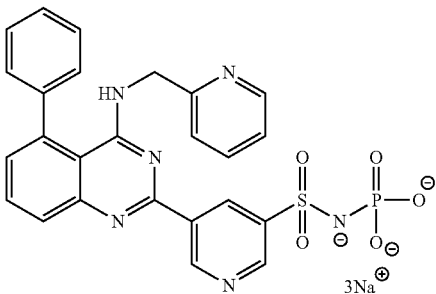

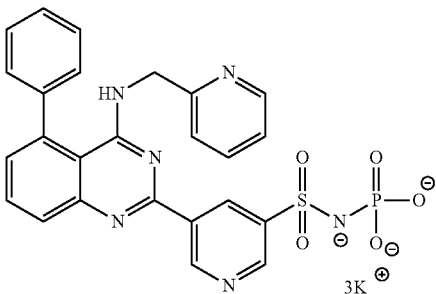

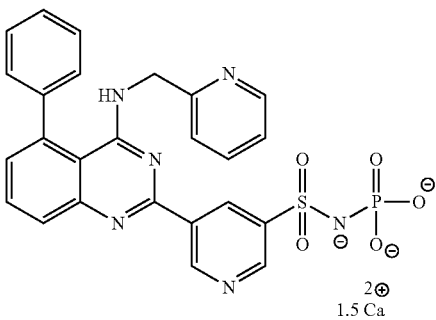

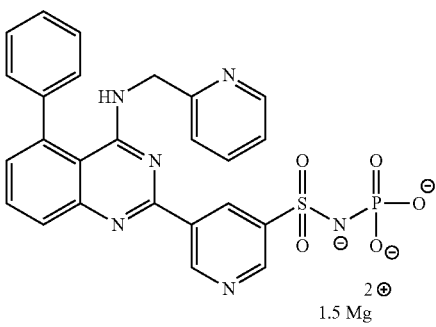

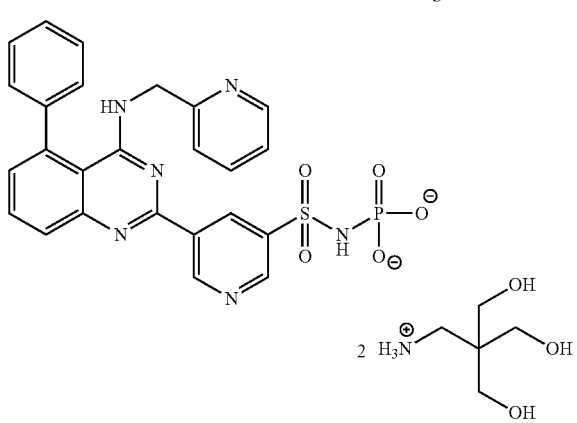

or tautomers thereof.

In fifth embodiment of the present disclosure, provides a compound of formula III

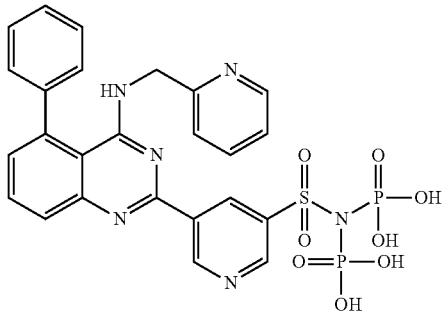

Formula III or pharmaceutically acceptable salt thereof

In sixth embodiment of the present disclosure, provides a pharmaceutical composition comprising a therapeutically effective amount of at least one compound of formula I or formula II.

In first embodiment of the sixth aspect, provides at least one other therapeutic agent.

In seventh embodiment of the present disclosure, provides a method of treating or preventing arrhythmia comprising administering to a patient in need thereof an effective amount of at least one compound of any one of structural formula I or structural formula II.

In eighth embodiment of the present disclosure, provides a method of controlling heart rate comprising administering to a patient in need thereof an effective amount of at least one compound of any one of structural formula I or structural formula II.

In ninth embodiment of the present disclosure, provides a method of treating an $I_{Kur}$-associated condition comprising administering to a patient in need thereof an effective amount of at least one compound of any one of structural formula I or structural formula II.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The abbreviations used in the present application, including particularly in the illustrative examples which follow, are well-known to those skilled in the art. Some of the abbreviations used are as follows:
Boc=tert-butyloxycarbonyl
AcOH or HOAc=acetic acid
$CH_2Cl_2$ or DCM=Dichloromethane
$CH_3CN$ or ACN=Acetonitrile
$CDCl_3$=deutero-chloroform
$CHCl_3$=Chloroform
$Cs_2CO_3$=cesium carbonate
DEA=Diethylamine
dil=dilute
DIPEA or Hunig's base=Diisopropylethylamine
DME=1,2-dimethyoxyethane
DMF=Dimethylformamide
DMSO=dimethyl sulfoxide
cDNA=complimentary DNA
EDTA=ethylenediaminetetraacetic acid
$Et_3N$ or TEA=Triethylamine
EtOAc=ethyl acetate
$Et_2O$=diethyl ether
EtOH=Ethanol
eq=equivalents
HCl=hydrochloric acid
$H_2SO_4$=sulfuric acid
$K_2CO_3$=potassium carbonate
KOAc=potassium acetate
$K_3PO_4$=potassium phosphate
LiOH=lithium hydroxide
MeOH=Methanol
min=minute or minutes
$MgSO_4$=magnesium sulfate
NaCl=sodium chloride
NaH=sodium hydride
$NaHCO_3$=sodium bicarbonate
$Na_2CO_3$=sodium carbonate
NaOH=sodium hydroxide
$Na_2SO_3$=sodium sulfite
$Na_2SO_4$=sodium sulfate
$NH_3$=Ammonia
$NH_4Cl$=ammonium chloride
$NH_4OH$=ammonium hydroxide
PG=protecting group
$POCl_3$=phosphorus oxychloride
i-PrOH or IPA=Isopropanol
PS=Polystyrene
$SiO_2$=silica oxide
$SnCl_2$=tin(II) chloride
TFA=trifluoroacetic acid
THF=Tetrahydrofuran The following Examples are offered to illustrate, but not limit, some of the preferred embodiments of the present disclosure and are not meant to be limiting of the scope of the disclosure. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

General Methods

The following methods were used in the working Examples, except where noted otherwise.

Analytical HPLC and HPLC/MS methods employed in characterization of the examples are as follows:

Reverse phase analytical HPLC/MS was performed on Shimadzu LC10AS systems coupled with Waters ZMD Mass Spectrometers or Waters AQUITY® system coupled with a Waters MICROMASS® ZQ Mass Spectrometer.
Method A:
  Linear gradient of 0 to 100% B over 3.2 min, with 1.5 min hold at 100% B;
  UV visualization at 220 nm;
  Column: Ascentis Express C18 (5×2.1 mm, 2.7 µm);
  Flow rate: 1 mL/min;
  Mobile Phase A: 10 mM $NH_4COOH$, 98% water, 2% acetonitrile;
  Mobile Phase B: 10 mM $NH_4COOH$, 2% water, 98% acetonitrile.

Method B:
  Linear gradient of 10 to 100% B over 15 min, with 12 min hold at 100% B;
  UV visualization at 220 nm;
  Column: XBridge phenyl (4.6×150 mm) 3.5 micron SC/1072;
  Flow rate: 1 mL/min;
  Buffer: 0.05% TFA in water pH 2.5
  Mobile Phase A: Buffer: acetonitrile (95:5);
  Mobile Phase B: acetonitrile: Buffer (95:5).
Method C:
  Linear gradient of 10 to 100% B over 15 min, with 12 min hold at 100% B;
  UV visualization at 220 nm;
  Column: SUNFIRE C18 (4.6×150 mm) 3.5 micron SC/862;
  Flow rate: 1 mL/min;
  Buffer: 0.05% TFA in water pH 2.5
  Mobile Phase A: Buffer: acetonitrile (95:5);
  Mobile Phase B: acetonitrile: Buffer (95:5).
Method D:
  Linear gradient of 0 to 100% B over 2 min;
  UV visualization at 220 nm;
  Column: PUROSPHER@star RP-18 (5×55 mm, 3 µm);
  Flow rate: 2.5 mL/min;
  Buffer: 10 mM $NH_4OAc$ in water;
  Mobile Phase A: Buffer: acetonitrile (90:10);
  Mobile Phase B: acetonitrile: Buffer (10:90).
Method E:
  Linear gradient of 0 to 100% B over 23 min, with 18 min hold at 100% B;
  UV visualization at 220 nm;
  Column: XBridge phenyl (4.6×150 mm) 3.5 micron;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method F:
  Linear gradient of 10 to 100% B over 30 min, with 25 min hold at 100% B;
  UV visualization at 220 nm;
  Column: XBridge phenyl (4.6×150 mm), 3.5 micron;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method G:
  Linear gradient of 10 to 100% B over 30 min, with 25 min hold at 100% B;
  UV visualization at 220 nm;
  Column: SUNFIRE C18 (4.6×150 mm) 3.5 micron;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method H:
  Linear gradient of 10 to 100% B over 15 min, with 12 min hold at 100% B;
  UV visualization at 220 nm;
  Column: XBridge phenyl (4.6×150 mm) 3.5 micron SC/749;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method I:
  Linear gradient of 0 to 100% B over 3.2 min, with 1.5 min hold at 100% B;
  UV visualization at 220 nm;
  Column: Ascentis Express C8 (5×2.1 mm, 2.7 µm);
  Flow rate: 1 mL/min;
  Mobile Phase A: 10 mM $NH_4COOH$, 98% water, 2% acetonitrile;
  Mobile Phase B: 10 mM $NH_4COOH$, 2% water, 98% acetonitrile.
Method J:
  Linear gradient of 10 to 100% B over 30 min, with 25 min hold at 100% B;
  UV visualization at 220 nm;
  Column: SUNFIRE C18 (4.6×150 mm) 3.5 micron SC/862;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method K:
  Linear gradient of 10 to 100% B over 15 min, with 12 min hold at 100% B;
  UV visualization at 220 nm;
  Column: XBridge phenyl (4.6×150 mm) 3.5 micron;
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).
Method L:
  Linear gradient of 0 to 100% B over 2.5 min, with 2 min hold at 100% B;
  UV visualization at 220 nm;
  Column: PUROSPHER@star RP-18 (4×55 mm, 3 µm);
  Flow rate: 2.5 mL/min;
  Buffer: 20 mM $NH_4OAc$ in water;
  Mobile Phase A: Buffer: acetonitrile (90:10);
  Mobile Phase B: acetonitrile: Buffer (10:90).
Method M:
  Linear gradient of 10 to 100% B over 30 min, with 25 min hold at 100% B;
  UV visualization at 220 nm;
  Column: Eclipse XDB C18 (150×4.6 mm, 3.5 µm);
  Flow rate: 1.0 mL/min;
  Mobile Phase A: 20 mM $NH_4OAc$ in water;
  Mobile Phase B: acetonitrile.
Method N:
  Linear gradient of 0 to 100% B over 2 min, with 3 min hold at 0% B;
  UV visualization at 220 nm;
  Column: ZORBAX® SB C18 (50×4.6 mm, 5 µm);
  Flow rate: 5.0 mL/min;
  Mobile Phase A: 10% MeOH-90% $H_2O$-0.1% TFA;
  Mobile Phase B: 90% MeOH-10% $H_2O$-0.1% TFA.
Method O:
  Linear gradient of 10 to 100% B over 15 min, with 12 min hold at 100% B;
  UV visualization at 220 nm;
  Column: SUNFIRE C18 (4.6×150 mm, 3.5 micron);
  Flow rate: 1 mL/min;
  Buffer: 0.05% TFA in water pH 2.5;
  Mobile Phase A: Buffer: acetonitrile (95:5);
  Mobile Phase B: acetonitrile: Buffer (95:5).

$^1$H NMR spectra were obtained with Bruker or JEOL FOURIER® transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

EXAMPLE 1

5-(5-Phenyl-4-(pyridin-2-ylmethylamino)quinazolin-2-yl)pyridin-3-ylsulfonylphosphoramidic acid (2)

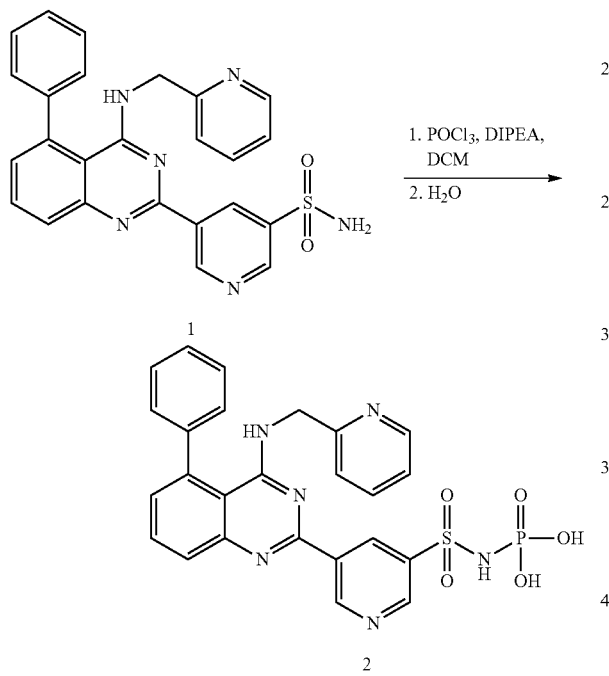

The preparation of 5-(5-phenyl-4-((pyridin-2-ylmethyl)amino)quinazolin-2-yl)pyridine-3-sulfonamide (1) may be found in WO 2011/028741.

To a solution of 5-(5-phenyl-4-((pyridin-2-ylmethyl)amino)quinazolin-2-yl)pyridine-3-sulfonamide (1) (3.0 g, 6.4 mmol) in DCM (50 mL) was added DIPEA (2.237 mL, 12.81 mmol) and the reaction mixture was stirred for 20 min. POCl$_3$ (2.39 mL, 25.6 mmol) was added at 0° C. and the reaction mixture was stirred for 4 h. DCM and excess POCl$_3$ were removed under vacuum and the residue was dissolved in 100 mL of water and stirred for 1 h. The resulting solid was filtered and the solid washed with excess water and dried under vacuum to yield 5-(5-phenyl-4-(pyridin-2-ylmethylamino)quinazolin-2-yl)pyridin-3-ylsulfonylphosphoramidic acid (2) (2.5 g, 4.6 mmol, 71% yield, 97% purity, off white color).

Re-crystallization Process: To a solution of amorphous ((5-(5-phenyl-4-((pyridin-2-ylmethyl)amino)quinazolin-2-yl)pyridin-3-yl)sulfonyl)phosphoramidic acid (2) (6.00 g, 10.9 mmol) (HPLC Purity 97%) in DMSO (100 mL) was added water (40 mL) and the suspension stirred for 1 h. The resulting solid was filtered and washed several times with water and dried under vacuum to yield pure crystalline ((5-(5-phenyl-4-((pyridin-2-ylmethyl)amino)quinazolin-2-yl)pyridin-3-yl)sulfonyl)phosphoramidic acid (2) (4.6 g, 8.4 mmol, 77% yield).

$^1$H NMR (400 MHz, DMSO-d$_6$) δ (ppm): 4.78 (d, J=4 Hz, 2H), 6.91 (t, J=4 Hz, 1H), 7.40-7.33 (m, 3H), 7.59-7.52 (m, 5H), 7.89-7.82 (m, 1H), 7.93 (dd, J=2.4 & 8.4 Hz, 1H), 8.35-8.33 (m, 1H), 9.09 (d, J=2.4 Hz, 1H), 9.28 (t, J=2 Hz, 1H), 9.75 (s, 1H). ESI MS+: 549. HPLC: purity 99.3%, retention time=6.30 min. Method B. MS Conditions: Mass Range: m/z 100-1200. Ionization and Mode: ESI+ Positive mode. Elemental analysis: MF $C_{25}H_{21}N_6O_5PS$. $4H_2O$, Calculated C, 48.57; H, 4.69; N, 13.53; S, 5.46; $H_2O$, 11.53. Found C, 48.26; H, 4.80; N, 13.19; S, 5.53; $H_2O$, 12.42.

EXAMPLE 2

Trisodium (5-(5-phenyl-4-((pyridin-2-ylmethyl)amino)quinazolin-2-yl)pyridin-3-yl)sulfonylphosphoramidate (3)

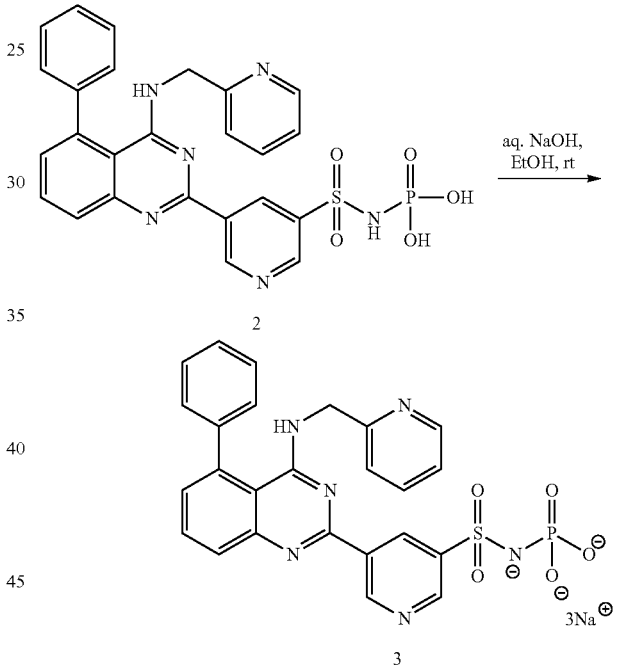

To a suspension of ((5-(5-phenyl-4-((pyridin-2-ylmethyl)amino)quinazolin-2-yl)pyridin-3-yl)sulfonyl)phosphoramidic acid (2) (0.030 g, 0.054 mmol) in ethanol (3 mL) was added NaOH (6.40 mg, 0.161 mmol) in 0.500 mL of water. The reaction mixture was stirred under nitrogen atmosphere at room temperature for 2 h. The reaction mixture was concentrated to dryness and the residue washed with ethyl acetate (2×8 mL), acetone (2×8 mL) and acetonitrile (2×8 mL) to afford trisodium (5-(5-phenyl-4-((pyridin-2-ylmethyl)amino)quinazolin-2-yl)pyridin-3-yl)sulfonylphosphoramidate (3) (0.028 g, 0.046 mmol, 85% yield) as a pink solid. $^1$H NMR (400 MHz, deuterium oxide) δ (ppm) 4.54 (s, 2H), 7.11 (d, J=7.78 Hz, 1H), 7.18-7.26 (m, 2H), 7.28-7.41 (m, 5H), 7.61-7.79 (m, 3H), 8.28 (d, J=4.52 Hz, 1H), 8.89-8.95 (m, 1H), 9.08 (d, J=2.01 Hz, 1H), 9.20 (d, J=1.76 Hz, 1H); LCMS Method D: retention time 1.24 min, [M+1]=469. HPLC Method C: Purity 95.1%, retention time 6.18 min, HPLC

EXAMPLE 3

Disodium (5-(5-phenyl-4-((pyridin-2-ylmethyl)amino)quinazolin-2-yl)pyridin-3-yl)sulfonylphosphoramidate (4)

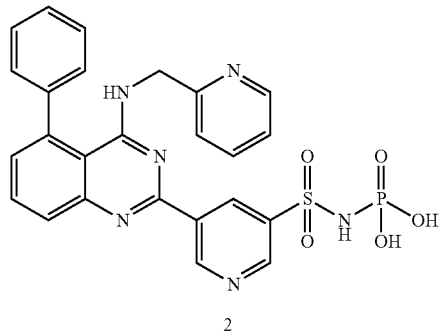

To a suspension of ((5-(5-phenyl-4-((pyridin-2-ylmethyl)amino)quinazolin-2-yl)pyridin-3-yl)sulfonyl)phosphoramidic acid (2) (0.070 g, 0.13 mmol) in ethanol (5 mL) was added NaOH (9.95 mg, 0.249 mmol) in 1 mL of water. The reaction mixture was stirred under nitrogen atmosphere at room temperature for 2 h. The reaction mixture was concentrated to dryness and the residue washed with ethyl acetate (2×10 mL), acetone (2×10 mL) and acetonitrile (2×15 mL) to afford disodium (5-(5-phenyl-4-((pyridin-2-ylmethyl)amino)quinazolin-2-yl)pyridin-3-yl)sulfonylphosphoramidate (4) (0.040 g, 0.068 mmol, 52% yield) as a yellow solid. $^1$H NMR (400 MHz, deuterium oxide) δ (ppm) 4.46 (s, 2H), 7.04 (d, J=7.78 Hz, 1H), 7.16 (d, J=6.27 Hz, 1H), 7.18-7.23 (m, 1H), 7.26 (d, J=6.27 Hz, 2H), 7.33 (d, J=6.78 Hz, 3H), 7.57-7.72 (m, 3H), 8.27 (d, J=4.27 Hz, 1H), 8.88 (br. s., 1H), 9.03 (s, 1H), 9.19 (s, 1H); $^{31}$P (162.0 MHz, DMSO-d$_6$) δ (ppm) −5.19; LCMS Method I: retention time 1.61 min, [M+1]=549. HPLC Method K: Purity 94%, retention time 8.59 min. Elemental analysis: MF C$_{25}$H$_{19}$N$_6$SPO$_5$.2.3 Na.3.8 H$_2$O, Calculated C, 45.03; H, 4.02; N, 12.60; Na, 7.79; H$_2$O, 10.27; Found C, 44.90; H, 3.58; N, 12.40; Na, 7.79; H$_2$O, 10.61.

EXAMPLE 4

Tris-(5-(5-phenyl-4-((pyridin-2-ylmethyl)amino)quinazolin-2-yl)pyridin-3-yl)sulfonylphosphoramidate (5)

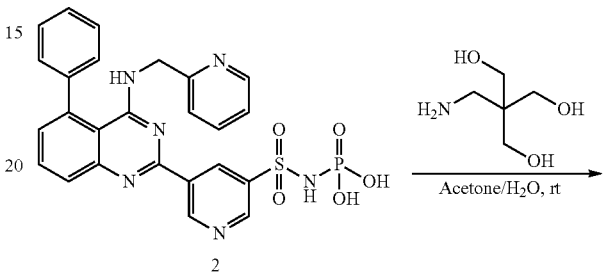

To a suspension of ((5-(5-phenyl-4-((pyridin-2-ylmethyl)amino)quinazolin-2-yl)pyridin-3-yl)sulfonyl)phosphoramidic acid (2) (0.030 g, 0.054 mmol) in acetone/water (2:2 mL) was added 2-amino-2-hydroxymethyl-propane-1,3-diol (0.012 g, 0.11 mmol). The resulting mixture was stirred under nitrogen atmosphere at room temperature for 2 h. The reaction mixture was concentrated to dryness and the residue was washed with ethyl acetate (2×8 mL), acetone (2×8 mL) to yield tris-(5-(5-phenyl-4-((pyridin-2-ylmethyl)amino)quinazolin-2-yl)pyridin-3-yl)sulfonylphosphoramidate (5) (0.028 g, 0.034 mmol, 64% yield) as a white solid. $^1$H NMR (400 MHz, deuterium oxide) δ ppm 3.56 (s, 12H), 4.62 (s, 2H), 7.22 (d, J=8.03 Hz, 1H), 7.25-7.29 (m, 1H), 7.33 (d, J=6.53 Hz, 1H), 7.38-7.45 (m, 5H), 7.71 (t, J=7.78 Hz, 2H), 7.77-7.86 (m, 1H), 8.34 (d, J=5.02 Hz, 1H), 8.96 (s, 1H), 9.09 (d, J=2.01 Hz, 1H), 9.30 (s, 1H). LCMS Method A: retention time 1.60 min, [M+1]=549. HPLC Method K: Purity 94.6%, retention time 6.41 min, HPLC Method C: Purity 95.0%, retention time 6.35 min.

EXAMPLE 5

Tripotassium (5-(5-phenyl-4-((pyridin-2-ylmethyl)amino)quinazolin-2-yl)pyridin-3-yl)sulfonylphosphoramidate (6)

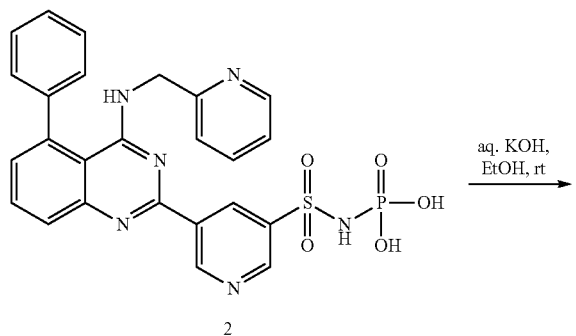

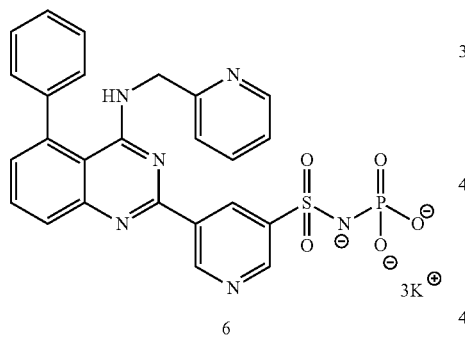

To a suspension of ((5-(5-phenyl-4-((pyridin-2-ylmethyl)amino)quinazolin-2-yl)pyridin-3-yl)sulfonyl)phosphoramidic acid (2) (0.030 g, 0.054 mmol) in ethanol (3 mL) was added KOH (9.0 mg, 0.16 mmol) in 0.5 mL of water. The resulting mixture was stirred under nitrogen atmosphere at room temperature for 2 h. The reaction mixture was concentrated to dryness and the residue was washed with ethyl acetate (2×8 mL), acetone (2×8 mL) and acetonitrile (2×8 mL) to afford tri-potassium(5-(5-phenyl-4-((pyridin-2-ylmethyl)amino)quinazolin-2-yl)pyridin-3-yl)sulfonylphosphoramidate (6) (0.028 g, 0.043 mmol, 78% yield) as a brown solid. $^1$H NMR (400 MHz, deuterium oxide) δ ppm 4.52 (s, 2H), 7.09 (d, J=7.78 Hz, 1H), 7.19-7.24 (m, 2H), 7.28-7.40 (m, 5H), 7.61-7.77 (m, 3H), 8.28 (d, J=4.27 Hz, 1H), 8.91 (t, J=1.88 Hz, 1H), 9.08 (d, J=2.26 Hz, 1H), 9.21 (d, J=1.76 Hz, 1H); LCMS Method A: retention time 1.60 min, [M+1]=549.2. HPLC Method B: Purity 96.0%, retention time 6.09 min, HPLC Method C: Purity 96.0%, retention time 5.86 min. Elemental analysis: MF $C_{25}H_{18}N_6SPO_5$·2.6 K·4.5 $H_2O$, Calculated C 41.22; H, 3.72; N, 11.54; K, 14.12; $H_2O$, 11.00; Found C, 40.79; H, 3.56; N, 11.17; K, 13.76; $H_2O$, 10.49.

EXAMPLE 6

Calcium (5-(5-phenyl-4-((pyridin-2-ylmethyl)amino)quinazolin-2-yl)pyridin-3-yl)sulfonylphosphoramidate (7)

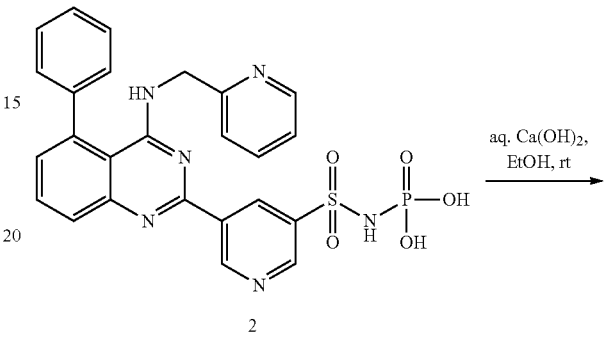

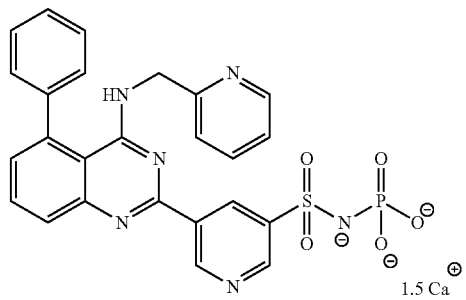

To a suspension of ((5-(5-phenyl-4-((pyridin-2-ylmethyl)amino)quinazolin-2-yl)pyridin-3-yl)sulfonyl)phosphoramidic acid (2) (0.200 g, 0.365 mmol) in ethanol (5 mL) was added calcium hydroxide (0.041 g, 0.55 mmol) in 2 mL of water. The resulting mixture was stirred under nitrogen atmosphere at room temperature for 2 h. The reaction mixture was concentrated to dryness and the residue was washed with ethyl acetate (2×10 mL), acetone (2×10 mL) and acetonitrile (2×15 mL) to afford calcium (5-(5-phenyl-4-((pyridin-2-ylmethyl)amino)quinazolin-2-yl)pyridin-3-yl)sulfonylphosphoramidate (7) (0.195 g, 0.322 mmol, 88.6% yield) as a white solid. $^1$H NMR (400 MHz, DMSO-$d_6$) δ (ppm) 4.77 (d, J=4.27 Hz, 2H), 6.92 (t, J=4.14 Hz, 1H), 7.26-7.35 (m, 2H), 7.39 (d, J=8.03 Hz, 1H), 7.50-7.60 (m, 5H), 7.79 (td, J=7.65, 1.76 Hz, 1H), 7.83-7.89 (m, 1H), 7.91-7.96 (m, 1H), 8.30 (d, J=4.27 Hz, 1H), 9.10 (s, 1H), 9.25 (t, J=2.13 Hz, 1H), 9.73 (d, J=2.01 Hz, 1H); LCMS Method I: retention time 1.66 min, [M−1]=547. HPLC Method B: Purity 94.3%, retention time 6.17 min, HPLC Method C: Purity 94.45%, retention time 5.97 min. Elemental analysis: Compound was hygroscopic, elemental analysis not obtained.

EXAMPLE 7

Magnesium (5-(5-phenyl-4-((pyridin-2-ylmethyl)amino)quinazolin-2-yl)pyridin-3-yl)sulfonylphosphoramidate (8)

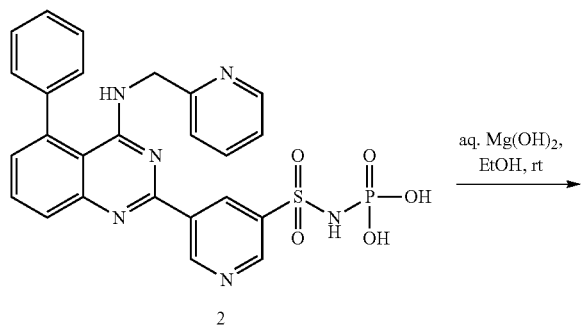

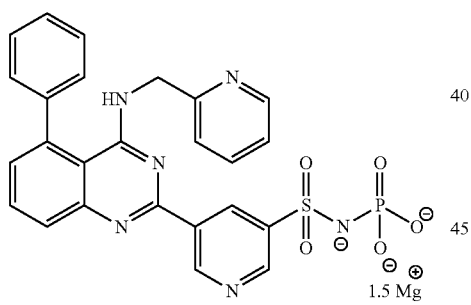

To a suspension of ((5-(5-phenyl-4-((pyridin-2-ylmethyl)amino)quinazolin-2-yl)pyridin-3-yl)sulfonyl)phosphoramidic acid (2) (0.050 g, 0.091 mmol) in ethanol (5 mL) was added magnesium hydroxide (7.97 mg, 0.137 mmol) in 1 mL of water. The resulting mixture was stirred under nitrogen atmosphere at room temperature for 2 h. The reaction mixture was concentrated to dryness and the residue was washed with ethyl acetate (2×5 mL), acetone (2×10 mL) and acetonitrile (2×10 mL) to afford magnesium(5-(5-phenyl-4-((pyridin-2-ylmethyl)amino)quinazolin-2-yl)pyridin-3-yl)sulfonylphosphoramidate (8) (0.040 g, 0.069 mmol, 76% yield) as a yellow solid. $^1$H NMR was not taken because of poor solubility. LCMS Method I: retention time 1.66 min, [M−1]=547. HPLC Method B: Purity 98.1%, retention time 6.18 min, HPLC Method C: Purity 95.6%, retention time 5.98 min. Elemental analysis: MF $C_{25}H_{20}N_6SPO_5 \cdot Mg \; H_2O$, Calculated C, 46.15; H, 4.41; N, 12.92; Mg, 4.15; $H_2O$, 11.70. Found C, 40.66; H, 4.12; N, 11.23; Mg, 4.14; $H_2O$, 11.70; C and N are not in agreement.

EXAMPLE 8

(5-(5-Phenyl-4-((pyridin-2-ylmethyl)amino)quinazolin-2-yl)pyridin-3-yl)sulfonyl)(phosphono)phosphoramidic acid (10

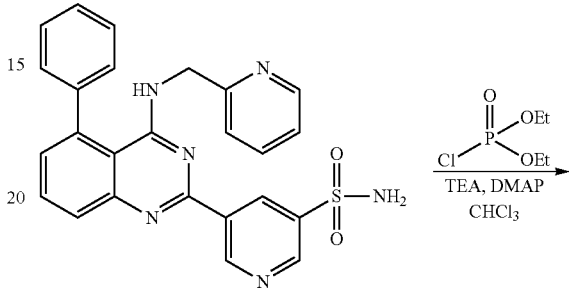

To a suspension of 5-(5-phenyl-4-(pyridin-2-ylmethylamino)quinazolin-2-yl)pyridine-3-sulfonamide (1) (0.150 g, 0.320 mmol) in CHCl$_3$ (10 mL) was added triethylamine (0.268 mL, 1.92 mmol) followed by 4-dimethylaminopyridine (7.8 mg, 0.064 mmol) under nitrogen atmosphere. The reaction mixture was stirred at 0° C. for 5 min and diethyl phosphorochloridate (0.331 g, 1.92 mmol) was added dropwise. The reaction mixture was allowed to warm up to room temperature and stirred overnight. The reaction mixture was diluted with DCM (20 mL) and water (20 mL), and extracted with DCM (3×50 mL). The combined organic layers were washed with water and brine and dried over $Na_2SO_4$, filtered and concentrated under reduced pressure. The residue was purified by HPLC purification to afford ethyl hydrogen diethoxyphosphoryl((5-(5-phenyl-4-((pyridin-2-ylmethyl)amino)quinazolin-2-yl)pyridin-3-yl)sulfonyl)phosphoramidate (9) (0.045 g, 0.063 mmol, 20% yield) as a yellow solid. Preparative (Water mass) HPLC Conditions: Column: Atlantis dc18 (19×250 mm) 10 µm, Mobile Phase A: 10 mm ammonium acetate. Mobile Phase B: acetonitrile, Gradient: 10 to 60% B over 10 min, Flow Rate: 15 mL/min., Retention time: 11.35 min.; $^1$H NMR (400 MHz, chloroform-d) (δ ppm) 1.20-1.34 (m, 9H) 4.06-4.22 (m, 6H) 4.60-4.77 (m, 2H) 6.63 (br. s., 1H) 7.09-7.20 (m, 3H), 7.44-7.54 (m, 5H) 7.61-7.72 (m, 2H) 7.85-7.96 (m, 1H) 8.42 (d, J=4.02 Hz, 1H) 9.21 (dd, J=6.78, 2.01 Hz, 2H) 9.67 (d, J=2.01 Hz, 1H); LCMS Method D: retention time 1.56 min, [M+1]=713.2.

To a suspension of ethyl hydrogen diethoxyphosphoryl((5-(5-phenyl-4-((pyridin-2-ylmethyl)amino)quinazolin-2-yl)pyridin-3-yl)sulfonyl)phosphoramidate (9) (0.040 g, 0.056 mmol) in DCM (5 mL) was added iodotrimethylsilane (0.067 g, 0.34 mmol) dropwise, under a nitrogen atmosphere at 0° C. The mixture was stirred for 2 h at 0° C. and the solvent was removed under reduced pressure. The residue was cooled to 0° C. and treated with a mixture of acetone (10 mL) and $H_2O$ (0.20 mL). After stirring at 0° C. for 1 h, the mixture was stirred at room temperature overnight. The resulting suspension was filtered and the solid was washed with acetone (20 mL), dried and purified by preparative HPLC to afford ((5-(5-phenyl-4-((pyridin-2-ylmethyl)amino)quinazolin-2-yl)pyridin-3-yl)sulfonyl)(phosphono)phosphoramidic acid (10) (0.025 g, 0.040 mmol, 71% yield) as a white solid. Preparative HPLC Conditions: Column: KROMASIL® C-4 (250× 21.2) mm, 5 µm, Mobile Phase A: 10 mM ammonium acetate in water, Mobile Phase B: acetonitrile, Gradient: 20 to 40% B over 7 min, 100% B for 12.5 min., Flow Rate: 17 mL/min., Retention time: 9 min.; $^1$H NMR (400 MHz, DMSO-$d_6$) δ (ppm) 4.78 (d, J=3.76 Hz, 2H), 6.96 (br. s., 1H), 7.23 (dd, J=6.53, 5.27 Hz, 1H), 7.31 (dd, J=7.03, 1.25 Hz, 1H), 7.41 (d, J=7.78 Hz, 1H), 7.51-7.61 (m, 5H), 7.73 (td, J=7.65, 1.76 Hz, 1H), 7.80-7.88 (m, 1H), 7.96 (dd, J=8.41, 1.13 Hz, 1H), 8.23 (d, J=4.27 Hz, 1H), 9.11 (d, J=2.01 Hz, 1H) 9.17 (t, J=2.01 Hz, 1H), 9.67 (d, J=2.01 Hz, 1H); $^{31}$P (162.0 MHz, DMSO-$d_6$) δ (ppm) −8.820, −8.917, −15.535, −15.629; LCMS Method I: retention time 1.56 min, [M−1]=627. HPLC Method H: Purity 95.0%, retention time 5.27 min.

Protocol for Solubility Studies of the Compounds of Instant Disclosure

The solubility of the compounds of the present invention have been evaluated at various pH levels. The solubility was tested using the procedure described below.

Excess amount of powder compound was equilibrated with 1 mL of buffer in a 2 mL glass vial and the dispersion of the compound in buffer ensured by vortexing, followed by sonication. The vials were shaken at 300 rpm at room temperature for 24 h. After 24 h incubation, the slurry was filtered and the filtrate analyzed by HPLC for the quantification of the solubilized fraction of compound using a four point calibration curve.

Note: The incubation time was decided based on the aqueous stability data. If the compound was stable in the buffer up to 24 hrs, then the solubility was measured after 24 hrs, otherwise kinetic solubility data is reported. The solubility data at different pH conditions at 24 h (mg/mL) is provided in below Table 1.

Using the test described above, the following data was generated.

TABLE 1

Solubility at different pH condiitions at 24 h (mg/mL)

| | Comp numbers | | | | | | | |
|---|---|---|---|---|---|---|---|---|
| | 1 free base | 2 Free acid* | 3 Na Salt* | 5 Di-Tris Salt | 6 K salt | 7 Ca Salt | 8 Mg Salt | 10 diphosphate |
| pH 1 | 6.4 | 0.25 | 0.75 | 1.62 | 0.29 | 0.99 | 0.6 | >1.74 |
| pH 2 | 0.41 | 0.03 | 0.11 | 0.08 | 0.09 | 0.12 | 0.02 | >4.05 |
| pH 3 | <0.001 | 0.01 | 0.02 | 0.03 | 0.07 | 0.02 | 0.02 | >2.11 |
| pH 5 | <0.001 | 0.002 | 0.15 | 0.022 | 0.25 | 0.07 | 0.03 | >5.12 |
| pH 6.5 | <0.001 | 0.11 | 4.62 | 2.023 | 0.3 | 1.15 | 0.16 | >4.58 |
| pH 7.4 | <0.001 | 0.56 | 7.3 | 2.514 | >1.07 | 2.41 | 0.19 | >1.99 |

*Crystalline Form

By improving the pH dependent solubility, the compounds of the present invention are able to overcome pH dependent absorption of the compound. Therefore, the absorption of the compound would not depend on variations in the stomach acid levels of the patient. Variations in the stomach pH may occur because of other medications or food that has been ingested. The compound would be absorbed more uniformly independent of the pH of the stomach.

Utility

The compounds of the present invention are useful as prodrugs of the compound (1). Compound (1) has been shown to be an $I_{Kur}$ inhibitor, as such, the compounds of the present invention are useful in the treatment of $I_{Kur}$ related disorders.

Assays to determine the degree of activity of a compound as an $I_{Kur}$ inhibitor are well known in the art and are described in references such as *J. Gen. Physiol.*, 101(4):513-543 (April 1993), and *Br. J. Pharmacol.*, 115(2):267-274 (May 1995).

Assays to determine the degree of activity of a compound as an inhibitor of other members of the $K_v1$ subfamily are also well known in the art. For example, inhibition of $K_v1.1$, $K_v1.2$ and $K_v1.3$ can be measured using procedures described by Grissmer, S. et al., *Mol. Pharmacol.*, 45(6):1227-1234 (June 1994); inhibition of $K_v1.4$ can be measured using procedures described by Petersen, K. R. et al., *Pflugers Arch.*, 437(3): 381-392 (February 1999); inhibition of $K_v1.6$ can be measured using procedures described by Bowlby, M. R. et al., *J. Neurophysiol.* 73(6):2221-2229 (June 1995); and inhibition of $K_v1.7$ can be measured using procedures described by Kalman, K. et al., *J. Biol. Chem.*, 273(10):5851-5857 (Mar. 6, 1998).

It is believed that $K_v1.5$ data ($IC_{50}$=46 nM) demonstrates the ability of Compound 1, and therefore, the compounds of the present disclosure acting as prodrugs for compound 1, to significantly increase the inhibition of the $K_v1.5$ channel of voltage-gated K+ channels. By displaying activity as inhibitors of the $K_v1.5$ channel of voltage-gated K+ channels, compounds of the present disclosure are expected to be useful in the treatment of human diseases associated with the $K_v1.5$ channel.

The phosphoramidic acid prodrugs of the present disclosure were subjected to in-vitro assays, cell based (path clamp) or isolated heart (Lagendorff), and was observed that the compounds of the present disclosure were converted to its parent compound in the presence of phosphatases present in these assays.

The in vivo models, rabbit PD models were used to study the compounds of the instant disclosure. The rabbit PD model was chosen as a bridging study for the prodrugs of the instant disclosure as the predominant expression of Ikur in rabbit and human atrium allows for meaningful pharmacodynamic and safety data for Ikur blockers. Particularly, the Rabbit Atrial Effective Refractory Period (AERP) model was used to study the compounds of instant disclosure. The in vivo models used for testing the compounds of instant disclosure has confirmed that the prodrugs of the instant disclosure effectively cleaves to respective parent compounds to provide the desired therapeutic activity of inhibiting the $I_{Kur}$.

Further, a single dose pharmacodynamic evaluation in rabbits indicated that the compounds of the present disclosure have similar in vivo pharmacology in the rabbit when compared to the parent form of the prodrugs.

Furthermore, a crossover study of Compound 1 and Compound 2 (as per Example 1) following single oral administration to non-naïve male cynomolgus monkeys with or without famotidine pretreatment Species: Male cynomolgus monkeys (N=5) previously characterized as famotidine responders were used for this study.

Study design: A four arm cross over study, with a 7-day wash out period in between treatments. Test compounds and famotidine were both administered in gelatin capsules. Dose of Compound 2 was 66.2 mg/capsule/animal, equivalent to 50 mg/capsule/animal of Compound 1. Physical form for both Compound 1 and Compound 2 was crystalline. D90, D50 & D10 for Compound 1 were 12.5, 4.8, and 1.2 micron, respectively. D90, D50 and D10 for Compound 2 were 13.9, 4, and 3.3 micron, respectively.

TABLE 2

| Phase | Treatment |
| --- | --- |
| I | Compound 1 (50 mg/capsule/animal) |
| II | Famotidine (40 mg/capsule/animal), given 3 h before Compound 1 (50 mg/capsule/animal) |
| III | Compound 2 (66.2 mg/capsule/animal) |
| IV | Famotidine (40 mg/capsule/animal), given 3 h before Compound 2 (66.2 mg/capsule/animal) |

Sampling time points: Blood samples were collected at 0 min (pre-dose), 15 min, 30 min, 45 min, 1 h, 2 h, 4 h, 6 h, 8 h, 24 h and 48 h post-dose.

Bioanalysis: The plasma samples were analyzed for the concentrations of Compound 1 and Compound 2, using scientifically validated bioanalytical methods.

PK analysis: Pharmacokinetic parameters Cmax, Tmax, and AUC (0-t) were calculated using a non-compartmental analysis method.

Cyno Famotidine Study: The observed bioavailability of Compound 1 in this study was 16% and the observed bioavaliablity of Compound 1 when dosed as the prodrug, Compound 2 was 83%. For Compound 1, the decrease in Cmax was 66-75% when the cynos were pre-treated with famotidine and the AUC(24 h) decreased 21-66%. For Compound 2 (measuring Compound 1), there was an observed decrease in Cmax −31 to 25% and AUC(24 h) decrease 2 to 15% when the cynos were pre-treated with famotidine. Cyno famotidine study: The bioavailability of Compound 1 in DIC was improved from 16 to 83% with Compound 2 dosing (at 10 mpk). Minimal change in Cmax and AUC of Compound 1 was observed with famotidine treatment, with Compound 2.

N-Sulfonylphosphoramidic acid prodrugs have an improved pH dependent solubility profile of Compound 1 (shown in example 1) with an excellent exposure at 5 mpk and 100 mpk crystalline suspension dose in rats with increased bioavailability and no significant level of circulating pro-drug observed. High dose rat PK studies (100 mpk) have been done and it was found that <1% of circulating pro-drug was observed.

The compounds of the present disclosure are capable of being given IV or PO to mitigate pH dependent solubility. The physical, chemical and solubility properties of these prodrugs can be further modulated by the choice of the counterion of the pharmaceutically acceptable salt.

The compounds of the present invention are prodrugs of compound (1). As such, the compounds of the present invention have utility in providing compound (1) as a therapeutic agent.

Compound (1) inhibits the $K_v1$ subfamily of voltage-gated K+ channels, and as such are believed to be useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents including maintaining normal sinus rhythm; angina pectoris including relief of Prinzmetal's symptoms, vasospastic symptoms and variant symptoms; gastrointestinal disorders including reflux esauphagitis, functional dyspepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As Compound (1) is an inhibitor of the $K_v1$ subfamily of voltage-gated K+ channels. Compound (1) is believed to be useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeic dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The Compound (1) is a suspected antiarrhythmic agents which is useful in the prevention and treatment (including partial alleviation or cure) of arrhythmias. As inhibitors of $K_v1.5$, compounds within the scope of the present disclosure are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the Compound (1) blocks $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esauphagitis, functional dyspepsia, constipation, asthma, and diabetes. Additionally, $K_v1.5$ is known to be expressed in the anterior pituitary. Thus, administration of an $I_{Kur}$ blocker can stimulate growth hormone secretion. $I_{Kur}$ inhibitors can additionally be useful in cell proliferative disorders such as leukemia, and autoimmune diseases such as rheumatoid arthritis and transplant rejection.

The present disclosure thus provides methods for the prevention or treatment of one or more of the aforementioned disorders, comprising the step of administering to a subject in need thereof an effective amount of at least one compound of the formula I, II, or III, preferably compounds exemplified in the examples, more preferably, Examples 1-8, even more preferably, Example 1. Other therapeutic agents such as those described below may be employed with the inventive compounds in the present methods. In the methods of the present disclosure, such other therapeutic agent(s) may be administered prior to, simultaneously with or following the administration of the compound(s) of the present disclosure.

Dosage and Formulation

The present disclosure also provides pharmaceutical compositions comprising at least one of the compounds of the formula I, II, III, preferably compounds exemplified in all the examples, more preferably, Example 1 or salts thereof capable of preventing or treating one or more of the aforementioned disorders in an amount effective thereof, and a pharmaceutically acceptable vehicle or diluents. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I, II, III, preferably compounds exemplified in all the examples, more preferably, Example 1, may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I, II, III, preferably compounds exemplified in all the examples, more preferably, Example 1, are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I, II, III, preferably compounds exemplified in all the examples, more preferably, Example 1, may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present disclosure may be determined by one of ordinary skill in the art, and includes exemplary dosage amounts for an adult human from about 0.001 to 100 mg/kg of body weight of active compound per day, which may be administered in a single dose or in the form of individual divided doses, such as from 1 to 4 times per day. The preferred human dose ranges from about 1 mg to about 10 mg one time a day and even more preferred ranges from about 2 mg to about 6 mg one time a day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present disclosure may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, CELEBREX®, VIOXX® and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captopril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thrombin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., QUESTRAN®); antiproliferative agents such as cyclosporin A, TAXOL®, FK 506, and adriamycin; antitumor agents such as TAXOL®, adriamycin, epothilones, cisplatin and carboplatin; anti-diabetic agents such as biguanides (e.g., metformin), glucosidase inhibitors (e.g., acarbose), insulins, meglitinides (e.g., repaglinide), sulfonylureas (e.g., glimepiride, glyburide and glipizide), biguanide/glyburide combinations (i.e., GLUCOVANCE®), thiozolidinediones (e.g., troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g., cilostazol), and PDE V inhibitors (e.g., sildenafil); protein tyrosine kinase inhibitors; steroidal anti-inflammatory agents such as prednisone, and dexamethasone; and other anti-inflammatory agents such as ENBREL®. The combinations can be co-formulated or in the form of kits packaged to provide appropriate dosages for co-administration.

The above other therapeutic agents, when employed in combination with the compounds of the present disclosure, may be used, for example, in those amounts indicated in the Physicians' Desk Reference (PDR) or as otherwise determined by one of ordinary skill in the art.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this disclosure has been described with an emphasis upon particular embodiments, it will be obvious to those of ordinary skill in the art that variations in the particular compounds and methods may be used and that it is intended that the disclosure may be practiced otherwise than as specifically described herein. Accordingly, this disclosure includes all modifications encompassed within the spirit and scope of the disclosure as defined by the claims that follow.

What is claimed is:

1. A compound of structural formula I

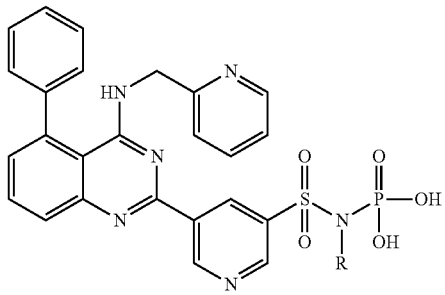

Formula I wherein R is H or —PO$_3$H or a pharmaceutically acceptable salt form thereof.

2. The compound of claim 1, wherein R is H, or pharmaceutically acceptable salt thereof.

3. The compound of claim 1, having structural formula II,

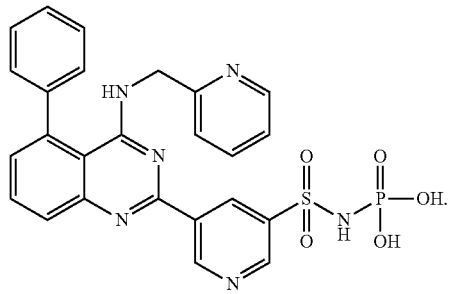

Formula II

4. The compound of claim 2, wherein the pharmaceutically acceptable salt is a counterion, and the counterion is Na$^+$, K$^+$, Ca$^{+2}$, Mg$^{+2}$, or (NH$_3^+$—CH$_2$—C (CH$_2$OH)$_3$.

5. The compound of claim 4, wherein the compound is selected from

-continued

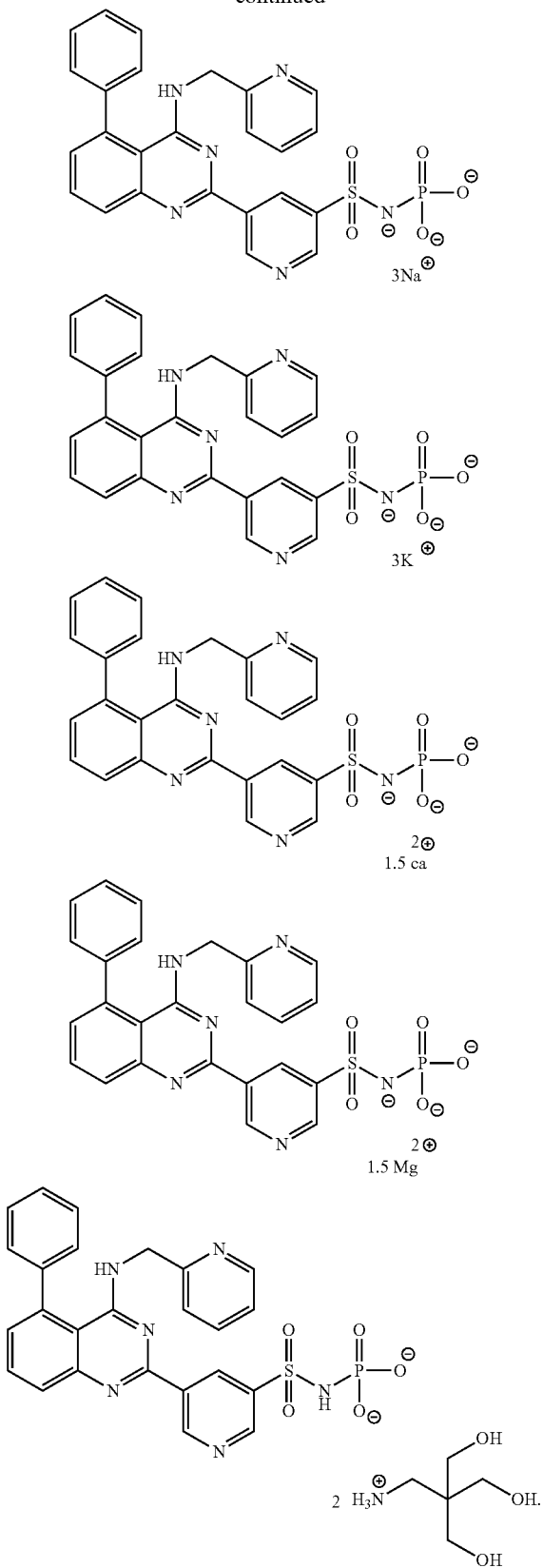

6. The compound of claim 1, wherein the compound is of formula III

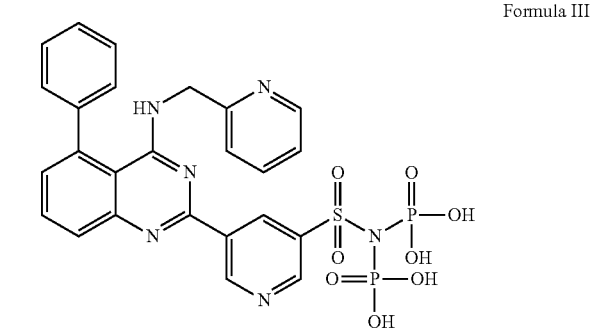 [SMILES: O=P(O)(O)N(P(=O)(O)O)S(=O)(=O)c1cncc(-c2nc(NCc3ccccn3)c3c(-c4ccccc4)cccc3n2)c1]

Formula III or pharmaceutically acceptable salt thereof.

7. A pharmaceutical composition comprising a therapeutically effective amount of at least one compound of claim 1, wherein the other therapeutic agent is selected from anti-arrhythmic agents, calcium channel blockers, anti-platelet agents, anti-hypertensive agents, anti thrombotic/anti thrombolytic agents, anti-coagulants, HMG-CoA reductase inhibitors, anti diabetic agents, thyroid mimetics, mineralocorticoid receptor antagonists, and cardiac glycosides.

8. The composition of claim 7, further comprising at least one other therapeutic agent.

9. A method of treating arrhythmia comprising administering to a patient in need thereof an effective amount of at least one compound of claim 1.

10. A method of controlling heart rate comprising administering to a patient in need thereof an effective amount of at least one compound of claim 1.

11. A pharmaceutical composition comprising a therapeutically effective amount of the compound of claim 3.

12. The composition of claim 11, further comprising at least one other therapeutic agent, wherein the other therapeutic agent is selected from anti-arrhythmic agents, calcium channel blockers, anti-platelet agents, anti-hypertensive agents, anti thrombotic/anti thrombolytic agents, anti-coagulants, HMG-CoA reductase inhibitors, anti diabetic agents, thyroid mimetics, mineralocorticoid receptor antagonists, and cardiac glycosides.

13. A method of treating arrhythmia comprising administering to a patient in need thereof an effective amount of the compound of claim 3.

14. A method of controlling heart rate comprising administering to a patient in need thereof an effective amount of the compound of claim 3.

15. A method of preventing arrhythmia in a patient having atrial fibrillation, comprising administering to a patient in need thereof an effective amount of at least one compound of claim 1.

16. A method of preventing arrhythmia in a patient having atrial fibrillation, comprising administering to a patient in need thereof an effective amount of at least one compound of claim 3.

* * * * *